United States Patent
Witt et al.

(10) Patent No.: US 8,297,936 B2
(45) Date of Patent: Oct. 30, 2012

(54) COMPENSATING TEMPERATURE-INDUCED ERRORS DURING PISTON MOVEMENT

(75) Inventors: Klaus Witt, Keltern (DE); Konstantin Choikhet, Karlsruhe (DE); Alexander Bierbaum, Karlsruhe (DE)

(73) Assignee: Agilent Technologies, Inc., Santa Clara, CA (US)

( * ) Notice: Subject to any disclaimer, the term of this patent is extended or adjusted under 35 U.S.C. 154(b) by 1443 days.

(21) Appl. No.: 11/900,578

(22) Filed: Sep. 12, 2007

(65) Prior Publication Data
US 2008/0080981 A1 Apr. 3, 2008

(30) Foreign Application Priority Data

Mar. 31, 2005 (EP) .................................... 05102533
Feb. 6, 2006 (WO) ................. PCT/EP2006/050709

(51) Int. Cl.
*F04B 49/10* (2006.01)
(52) U.S. Cl. ....... 417/32; 417/213; 73/61.52; 73/861.01
(58) Field of Classification Search .................... 417/32, 417/213; 73/61.52, 62.56, 61.57, 861.01, 73/861.02
See application file for complete search history.

(56) References Cited

U.S. PATENT DOCUMENTS

| | | | |
|---|---|---|---|
| 3,676,020 A | 7/1972 | Andreason et al. | |
| 4,032,445 A | 6/1977 | Munk | |
| 4,043,906 A | 8/1977 | Helmer | |
| 4,225,290 A | 9/1980 | Allington | |
| 4,406,158 A | 9/1983 | Allington | |
| 5,108,264 A * | 4/1992 | Abdel-Rahman | 417/20 |
| 5,450,743 A | 9/1995 | Buote | |
| 5,630,706 A | 5/1997 | Yang | |
| 2003/0052007 A1 | 3/2003 | Paul et al. | |
| 2004/0232080 A1 | 11/2004 | Neyer et al. | |
| 2006/0157392 A1* | 7/2006 | Best | 210/87 |
| 2008/0206067 A1* | 8/2008 | De Corral et al. | 417/53 |
| 2010/0189574 A1* | 7/2010 | Corral et al. | 417/53 |

FOREIGN PATENT DOCUMENTS

| | | |
|---|---|---|
| EP | 0 183 330 | 6/1986 |
| EP | 0309596 | 9/1987 |
| EP | 0 471 930 | 6/1991 |
| JP | 01083872 A | 3/1989 |
| WO | 03/079000 | 9/2003 |
| WO | 03079000 A1 | 9/2003 |

OTHER PUBLICATIONS

Zhou, X., et al., New Micro-Flow Pumping System for Liquid Chromatography, Journal of Chromatography A, 2001, pp. 165-171.
International Search Report Jun. 2, 2006.
Written Opinion dated Jun. 2, 2006.
Japanese Office Action for Application No. 2006-032194, mailed on Dec. 2, 2011 (7 pages).

\* cited by examiner

*Primary Examiner* — Charles Freay
*Assistant Examiner* — Patrick Hamo

(57) ABSTRACT

A method for controlling movement of a piston in a metering device is described. The method comprises supplying a fluid by actuating the metering device's piston, wherein compression or expansion of the fluid causes corresponding temperature variations. The method further comprises superposing a corrective movement onto the piston movement, with the corrective movement at least partly compensating for at least one of thermal expansion and contraction of the fluid induced by the temperature variations. In one embodiment, the corrective movement imposed onto the piston movement comprises two components: a reduction (74) of the compression jump (73), and a subsequent increase (75) of the piston's forward displacement rate (71) during a period (76) of time (72).

12 Claims, 10 Drawing Sheets

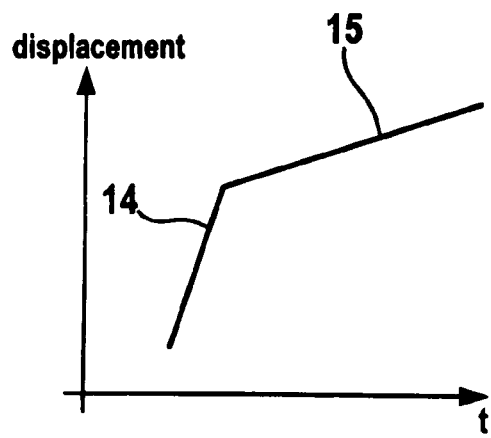
Fig. 1B
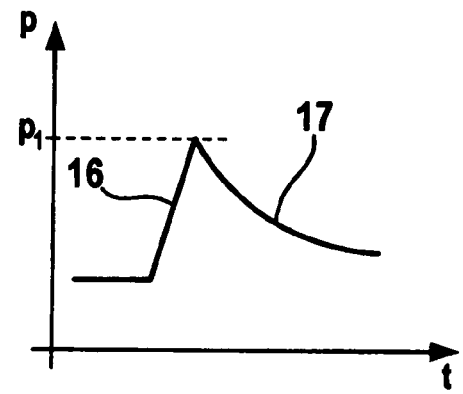
Fig. 1C
Fig. 2
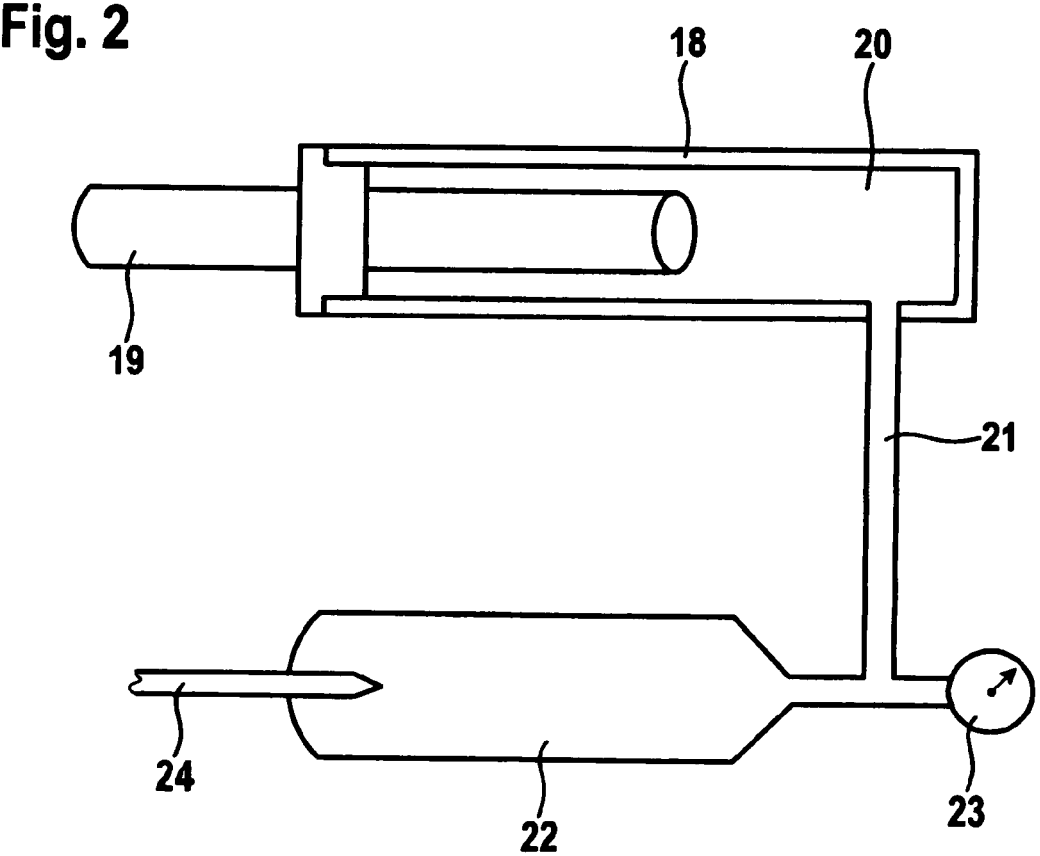

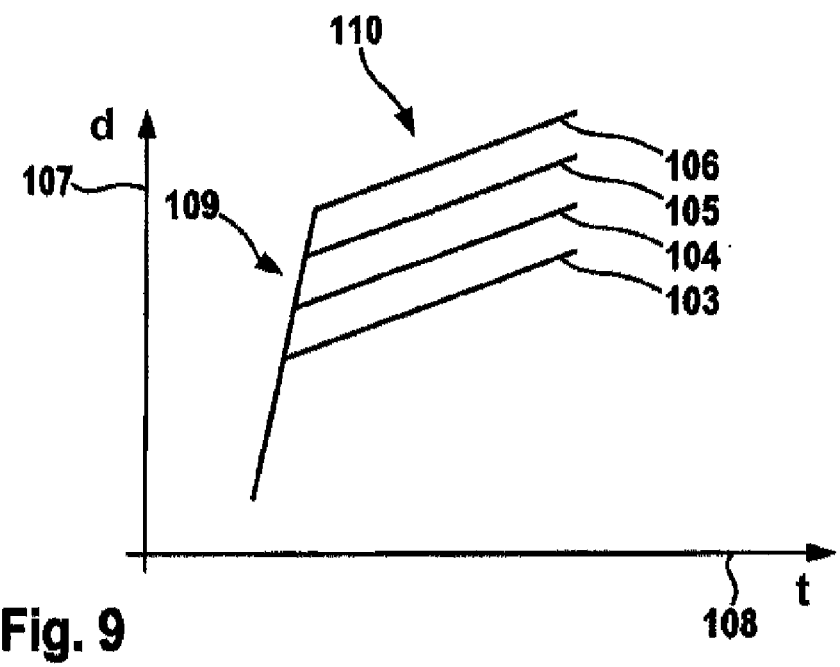
Fig. 9
Fig. 10
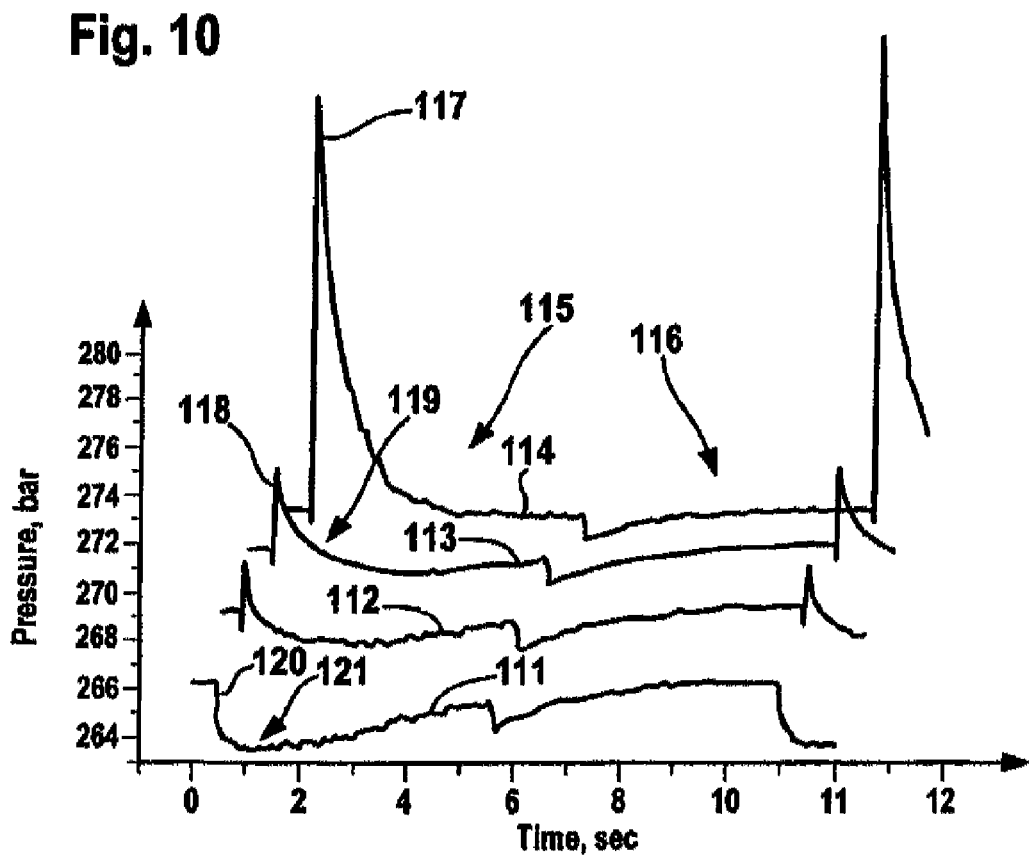

COMPENSATING TEMPERATURE-INDUCED ERRORS DURING PISTON MOVEMENT

This application is the National Stage of International Application No. PCT/EP2006/050709, Publication No. WO 2006/103133, International Filing Date, 6 Feb. 2006, which designated the United States of America, which is incorporated herein in its entirety.

BACKGROUND ART

The present invention relates to controlling movement of a piston in a metering device.

European Patent Application EP 87114091.9 relates to a pumping apparatus for delivering liquid at a high pressure, in particular for use in liquid chromatography. FIG. 12 shows a conventional liquid chromatography system 120, which comprises a pumping apparatus 121, a valve switch 127, a sample loop 126, a pre-column 128, a column 129, a detector 130, and a workstation 100. The pumping apparatus 121 comprises two pistons 122 which reciprocate in pump chambers, respectively. The output of the first pump chamber is connected via a valve to the input of the second pump chamber. The pistons are driven by linear drives, e.g. ball-screw spindles. The stroke volume displaced by the piston is freely adjustable by corresponding control of the angle by which the shaft of the drive motor is rotated during a stroke cycle. The control circuitry 123 is operative to reduce the stroke volume when the flow rate which can be selected by user at the user interface is reduced, thus leading to reduced pulsations in the outflow of the pumping apparatus.

European Patent Application EP 05102533.6 relates to controlling piston movement of a metering device, whereby compressibility effects due to pressure variations are taken into account. The piston's velocity is set to a desired flow rate and the solvent pressure is monitored. In case of pressure variations, a corrective movement that corresponds to the pressure-induced variation of the solvent volume in the supply flow path is superposed on the regular piston movement.

DISCLOSURE

It is an object of the invention to provide an improved volumetric metering by considering thermal effects. The object is solved by the independent claim(s). Further embodiments are shown by the dependent claim(s).

According to embodiments of the present invention, a method for controlling movement of a piston in a metering device comprises supplying a fluid by actuating the metering device's piston, wherein compression or expansion of the fluid causes corresponding temperature variations. The method further comprises superposing a corrective movement onto the piston movement, with the corrective movement at least partly compensating for at least one of thermal expansion and contraction induced by the temperature variations.

In high pressure fluidic systems, it might e.g. be required to supply small volumes of fluid at high pressure with great precision. In a metering device, the fluid is generally subjected to at least one of expansion and compression. An expansion might e.g. cause a temperature drop, whereas a compression might give rise to a temperature increase.

According to embodiments of the present invention, it is proposed to consider temperature-related effects like e.g. additional temperature-induced expansion or contraction of the fluid contained in the metering device. It is proposed to correct the piston's displacement-versus-time curve in accordance with the temperature-related effects. For example, corrective movements may be superposed onto the piston movement in a way that temperature-induced volumetric variations are compensated for. For example, in case of a temperature-induced volume expansion, one might impose a backward movement onto the piston, in order to at least partly compensate for the volume expansion. In case of a temperature-induced volume contraction, it might e.g. be suitable to superpose an additional forward displacement onto the piston movement, in order to counteract the volume contraction.

By taking the effects due to temperature variations into account and modifying the piston movement accordingly, it is possible to improve the precision of the solvent flow supplied by the metering device. Fluctuations and ripples due to temperature variations can be partly or entirely compensated for, and as a consequence, a stable flow of fluid can be supplied at a predefined flow rate with high precision. Especially in applications where metering devices are used for supplying small volumes of solvent at high pressure, the metering device's precision can be considerably improved.

It is often useful or required (e.g. in analytical applications) to provide a composite solvent with a predefined mixing ratio of two or more different solvents. For example, in applications related to sample analysis, a precisely defined mixing ratio of the composite solvent can be a prerequisite for obtaining reliable measurement results. Temperature-induced volumetric variations are capable of significantly disturbing the predefined mixing ratio by modulating the individual flow streams. By modifying the metering devices' piston movements in accordance with the temperature variations, a stable and precise mixing ratio of the composite solvent is obtained.

According to a preferred embodiment, at least one of temperature-induced flow variations and temperature-induced pressure variations of the fluid are at least partly compensated for by superposing the corrective movement onto the piston movement.

According to a preferred embodiment, the temperature variations of the fluid contained in the metering device's pump chamber might e.g. comprise instantaneous temperature changes that occur when compressing or expanding the fluid contained in the pump chamber. For example, when compressing the fluid, heat is generated, and the fluid's temperature is increased. When expanding the fluid contained in the metering device, the fluid is cooled down.

In addition to these instantaneous temperature changes, the temperature variations of the fluid contained in the pump chamber might e.g. comprise temperature equalization processes that occur subsequent to a temperature change. For example, after an instantaneous temperature change due to compression or expansion, there will be an exchange of thermal energy between the fluid contained in the pump chamber and the pump chamber's walls, and as a consequence, a temperature equalization is observed. For example, subsequent to a sudden temperature increase that is caused by a compression of the fluid, heat may be absorbed by the pump chamber's walls, and therefore, the sudden temperature increase related to the fluid's compression is followed by a slow temperature decline. Similarly, after a sudden temperature decrease, there might be a slow temperature increase related to a temperature equalization process.

Hence, there exist at least two different kinds of temperature variations: sudden temperature changes related to compression or expansion of the fluid, and subsequent temperature equalization processes that give rise to slow variations of the fluid's temperature.

According to a further embodiment, the metering device's duty cycle is characterized by a sequence of characteristic temperature variations. The temperature variations occurring during a duty cycle may be compensated for by modifying the piston's displacement-versus-time curve accordingly.

For example, at least some of the temperature variations give rise to corresponding thermal expansions or contractions of the fluid contained in the metering device. A sudden temperature change that is caused by a compression or expansion of the fluid in the metering device might e.g. give rise to an additional thermal expansion or contraction of the fluid. A temperature increase might e.g. cause an additional thermal expansion of the fluid in the metering device, whereas a temperature drop might lead to a thermal contraction of the fluid.

Alternatively or additionally, temperature equalization processes might cause thermal expansions or contractions of the fluid contained in the metering device. For example, if a temperature increase is followed by a slow temperature decline related to a temperature equalization process, there will be a slow thermal contraction of the fluid in the metering device. The other way around, if a sudden temperature drop is followed by a slow temperature equalization, there will be a slow thermal expansion of the fluid.

In a preferred embodiment, a thermal expansion or contraction related to a sudden temperature change is counteracted by superposing a corresponding sudden displacement component onto the piston movement.

In another preferred embodiment, a volumetric variation related to a temperature equalization process is counteracted by superposing a slow corrective movement pattern onto the piston movement.

According to a further preferred embodiment, a thermal expansion or contraction related to a temperature equalization process is counteracted by imposing an additional displacement rate onto the piston movement during a predefined period of time. Further preferably, the predefined period of time corresponds approximately to the period of time required for the temperature equalization process. For example, a slow volumetric shrinking might be compensated for by increasing the piston's forward displacement rate during a predefined or adapted period of time.

According to a preferred embodiment, the magnitude of the correction is chosen in dependence on the type of solvent contained in the metering device. Each solvent is characterized by its respective thermal properties, like e.g. thermal expansion coefficient, heat capacitance, thermal conductivity etc. under respective operating conditions. Such conditions may be, but are not limited to, absolute temperature, fluid density or absolute solvent pressure. With regard to different solvents, the extent of temperature-related effects varies strongly. For example, in case of water, temperature-induced effects are quite small. In case of an organic solvent like e.g. methanol, acetonitrile, or hexane, the effects related to thermal expansion (or contraction) are more pronounced. The magnitude of temperature related effects can be taken into account by varying the extent of the correction in dependence on the respective type of solvent in the metering device.

According to a further preferred embodiment, the time behaviour of the corrective movement is adjusted in dependence on the type of solvent contained in the pump chamber. The time required for temperature equalization strongly depends on a solvent's respective thermal properties, e.g. on the solvent's thermal conductivity and thermal capacity, and also e.g. on the thermal properties of the surrounding pump chamber. Furthermore, the time behaviour of the corrective movement might e.g. depend on the pump chamber's internal geometry.

In a preferred embodiment, a metering device is adapted for compressing a fluid contained in the pump chamber from atmospheric pressure to a pressure of up to several thousand bar, which corresponds to several hundred MPa. In a further preferred embodiment, the metering device is part of a microfluidic device. In microfluidic systems, dimensions get smaller and smaller, and the fluid volumes conveyed through the system become smaller and smaller as well. Correspondingly, fluid pressures may rise up to several hundred MPa. Hence, the effects due to temperature variations can become more and more pronounced and considering these is more important.

According to a preferred embodiment, the metering device comprises two pistons. A first piston is adapted for metering the fluid, wherein compression or expansion of the fluid in the pump chamber causes corresponding temperature variations. A second piston performs a corrective movement, in order to compensate for temperature-related effects. In particular, the second piston's corrective movement at least partly compensates for at least one of thermal expansion and contraction of the fluid induced by the temperature variations.

According to a preferred embodiment, the fluid system comprises a first fluid delivery line for supplying a first solvent to a mixing unit, a second fluid delivery line for supplying a second solvent to the mixing unit, and the mixing unit. The first fluid delivery line comprises a first metering device, and the second fluid delivery line comprises a second metering device. At the mixing unit's outlet, a composite solvent is supplied. By compensating for thermal expansions or contractions, the accuracy of the composite solvent's mixing ratio is considerably improved.

In a further preferred embodiment, the piston movements of the first and the second metering device are controlled in a way that the composite solvent's mixing ratio becomes substantially independent of temperature variations.

According to a further preferred embodiment, the composite solvent is supplied to a separation system adapted for separating compounds of a fluid sample. For this purpose, the mixing unit's outlet might be fluidically connected with the separation system's inlet. Then, the composite solvent is used as a mobile phase for separating compounds of a fluid sample. Further preferably, a solvent gradient is supplied to the separation system, e.g. to a separation column.

In a further preferred embodiment, the separation system is one of: a liquid chromatography system, an electrophoresis system, an electrochromatography system. The accuracy of analysis data acquired with a separation system of this type strongly depends on the accuracy of solvent composition. Therefore, by compensating for temperature-related effects, it is possible to improve the quality of the obtained data.

In a preferred embodiment, a fluid system comprises a primary piston pump and a secondary piston pump, with the primary piston pump and the secondary piston pump being fluidically connected in series. The pistons of the primary piston pump and the secondary piston pump are operated in an alternating manner. Thus, it is possible to provide a continuous flow of solvent over an extended period of time.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied for controlling an actuation mechanism for a metering device's piston.

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

FIG. 1(s) 1A, 1B, and 1C shows a high pressure fluid supply system;

FIG. 2 depicts a measurement set-up;

FIG. 4(s) 4A and 4B shows fluid pressure and temperature as a function of time for methanol;

FIG. 7(s) 7A and 7B depicts two alternative ways of correcting the piston movement;

FIG. 9 shows four different displacement-versus-time curves of a piston;

FIG. 10 illustrates four different pressure curves that correspond to the piston movement schemes of FIG. 9.

DETAILED DESCRIPTION OF THE PREFERRED EMBODIMENTS

Figure 1A:
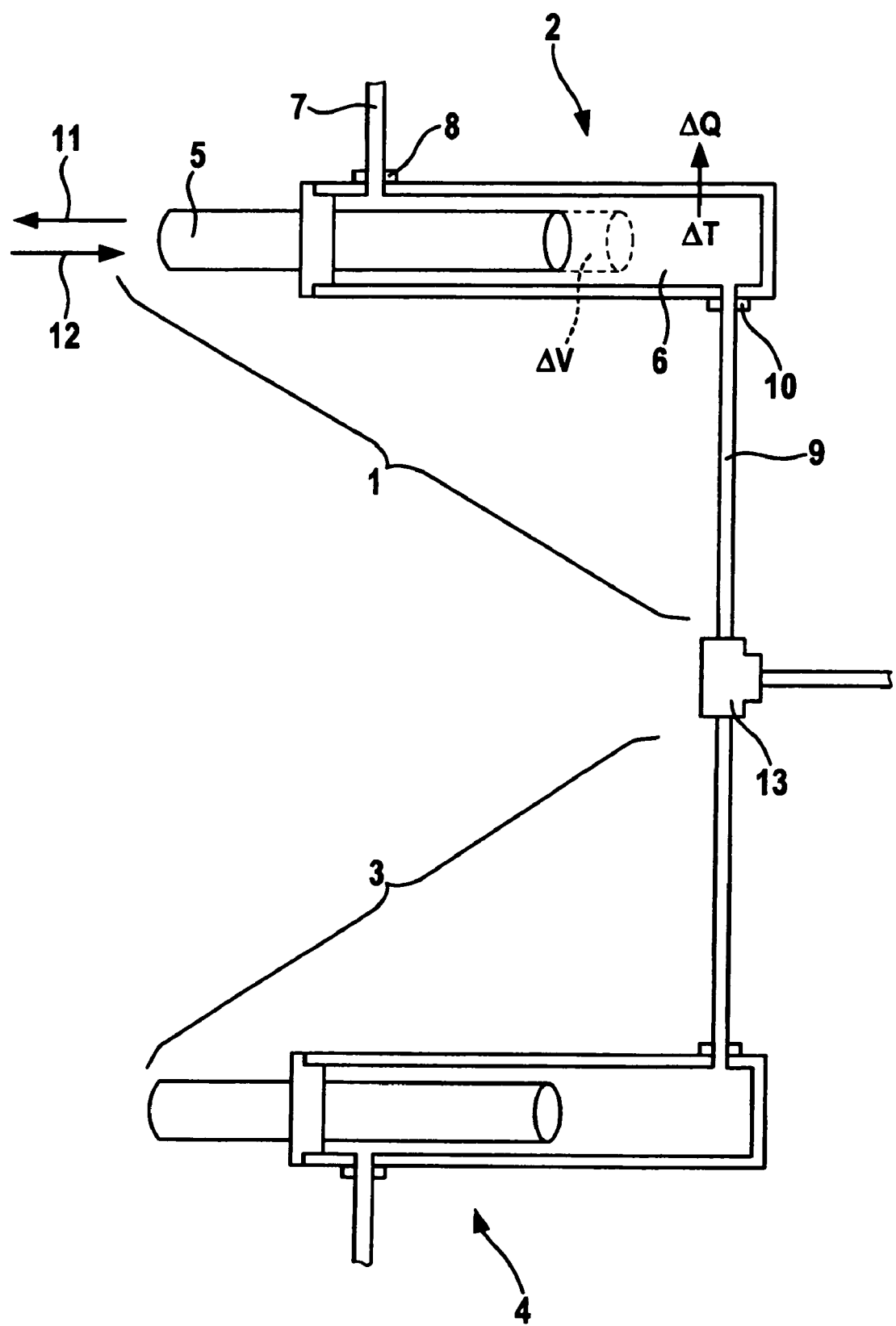

FIG. 1A shows a high-pressure fluid supply system comprising a first fluid supply path 1 with a piston pump 2, and a second fluid supply path 3 with a piston pump 4. The piston pump 2 comprises a piston 5 that reciprocates in a piston chamber 6. The piston pump 2 further comprises an inlet 7 with an inlet valve 8, and an outlet 9 with an outlet valve 10. During the piston's downwards stroke 11, the inlet valve 8 is open, and fluid is aspirated via the inlet 7. At the end of the downwards stroke 11, the pump chamber 6 is filled with fluid at atmospheric pressure. Then, during the piston's upwards stroke 12, it is often necessary to compress the fluid to a pressure of up to several thousand bar before supplying the fluid to a high-pressure mixing unit 13.

FIG. 1B shows a diagram of the piston's position as a function of time during the piston's upwards stroke 12. In order to compress the fluid contained in the pump chamber 6, the piston's actuation mechanism is adapted for imposing a well-defined jump 14 onto the piston's displacement. Due to this sudden change of the piston's position, the pressure of the fluid contained in the pump chamber 6 is increased to a desired pressure, e.g. to a pressure between 200 bar and 1200 bar. As soon as the pressure of the fluid contained in the pump chamber reaches system pressure, the outlet valve 10 opens, and fluid is supplied to the mixing unit 13 at a predefined rate. For supplying fluid at a predefined flow rate, the piston 5 is steadily moved forward with constant velocity. In the piston's displacement-versus-time diagram of FIG. 1B, this linear movement 15 is indicated. Hence, the piston's upwards stroke 12 comprises a jump 14 followed by a linear movement 15.

During the jump 14 of the piston position, the fluid contained in the fluid chamber 6 is compressed by a volume ΔV, which depends e.g. on the pressure increase Δp and on the fluid's compressibility κ. In FIG. 1A, the volume ΔV is indicated. The fluid is compressed almost adiabatically, and hence, there is almost no heat dissipation during the fluid's compression. The piston's mechanical work is almost entirely converted into heat. When compressing the fluid contained in the pump chamber 6 to a pressure of up to several thousand bar, which corresponds to several hundred MPa, the fluid heats up considerably, and a temperature increase ΔT is observed.

Because of thermal expansion, this temperature increase ΔT of the fluid might e.g. give rise to an additional contribution to the fluid's pressure. In FIG. 1C, the pressure p of the fluid contained in the pump chamber 6 is shown as a function of time. During the jump 14 of the piston position, a corresponding increase 16 of the fluid's pressure is observed. The temperature increase ΔT causes an expansion of the fluid contained in the pump chamber 6, and this expansion gives rise to an additional temperature-induced contribution Δp to the fluid's pressure. Hence, the pressure $p_1$ at the end of the sudden compression is partly due to the volumetric compression itself, and partly due to an expansion related to the temperature increase ΔT. In other words, at the end of the piston's jump 14, the pressure $p_1$ is higher than it is actually supposed to be considering just compressibility, because the temperature increase ΔT contributes to the obtained pressure.

During the subsequent linear movement 15 of the piston, the fluid contained in the pump chamber 6 slowly cools down, because heat slowly dissipates via the pump chamber's walls. In FIG. 1A, this heat dissipation ΔQ is indicated. The fluid's temperature slowly approaches the temperature of the surrounding pump chamber. The time behaviour of the temperature equalization process is closely related to thermal properties of the fluid, such as e.g. thermal conductivity and heat capacitance. When the fluid contained in the pump chamber 6 is cooled down, it contracts, and a slow decrease of the fluid's pressure is observed. Thus, the temperature equalization process leads to a corresponding pressure relaxation. The pressure-versus-time diagram of FIG. 1C depicts this pressure relaxation 17, which occurs during the piston's linear movement 15.

The temperature variations during a pump's duty cycle give rise to at least one of pressure variations and flow variations, which may affect the flow rate generated by the pump. Furthermore, in high-pressure mixing systems adapted for mixing two or more solvents, temperature-induced expansion or contraction translates to corresponding variations of solvent composition, which in turn affect the accuracy of the acquired data. For example, in liquid chromatography or electrochromatography systems, reliability of the acquired data strongly depends on the precision of the solvent gradients, and even small disturbances of solvent composition lead to non-negligible errors.

FIG. 2 shows a measurement set-up for investigating the effects of adiabatic compression or expansion. The set-up comprises a piston pump 18 with a piston 19 reciprocating in a pump chamber 20. The piston pump's outlet 21 is fluidly connected with a column tube 22. The fluid pressure in the column tube 22 is monitored using a suitable pressure sensor 23. The set-up further comprises a thermocouple 24 disposed in the column tube 22.

After filling the system with a solvent under investigation, the system is tightly sealed. Then, different compression jumps or expansion jumps are superposed onto the piston movement while recording the solvent's temperature and pressure as a function of time. Thus, measurements have been performed for different solvents, e.g. for water, methanol, acetonitrile, hexane.

Figure 3:
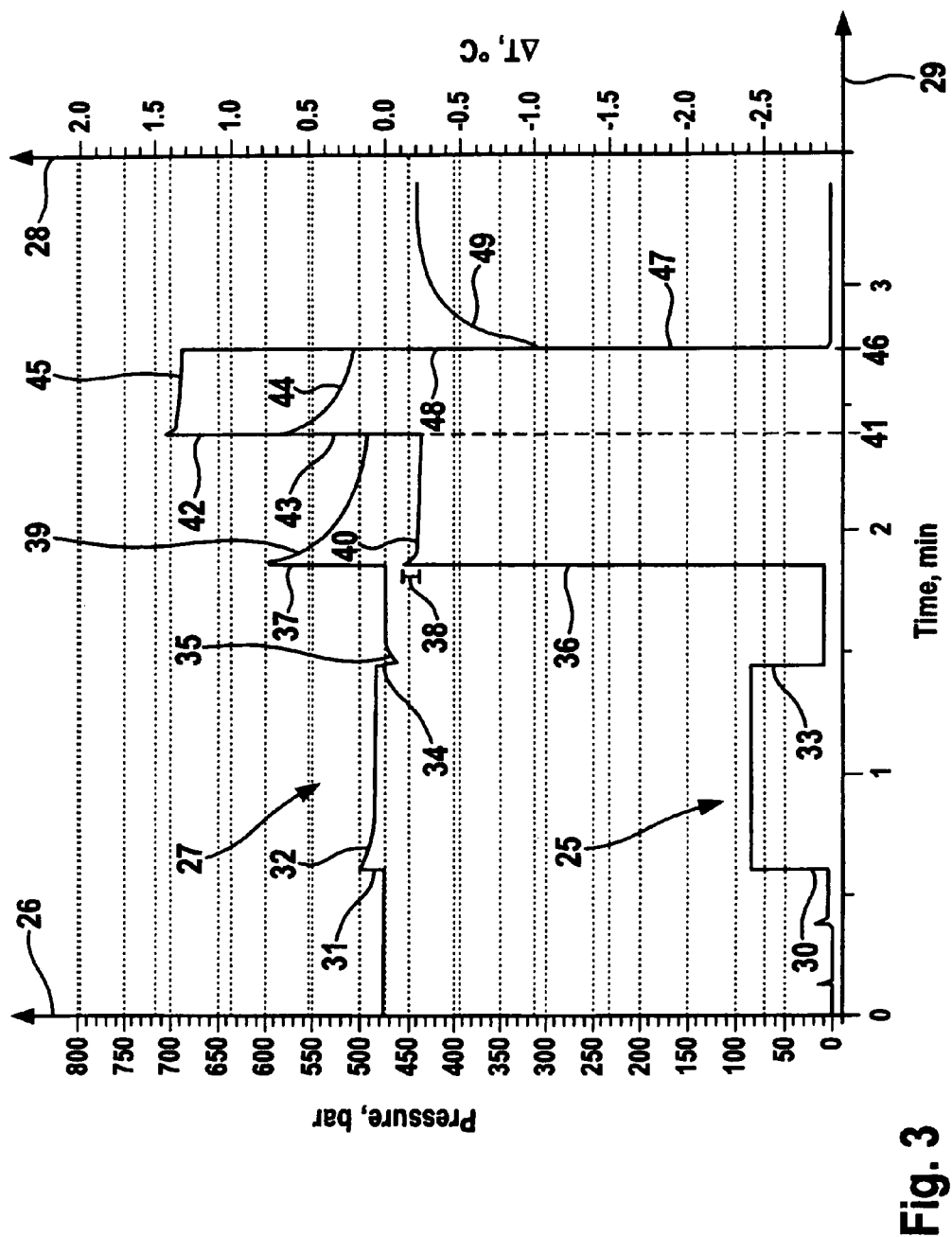
FIG. 3 shows fluid pressure and temperature as a function of time for water.

FIG. 3 shows results that have been obtained for water. Curve 25 shows fluid pressure as a function of time. The left-hand ordinate axis 26 indicates the fluid's pressure (in bar). Curve 27 depicts the fluid's temperature changes as a function of time, and the right-hand ordinate axis 28 indicates the magnitude of the respective temperature change ΔT (in ° C.). Time axis 29 shows the elapsed time (in minutes). When imposing a sudden forward movement onto the piston, an increase 30 of the fluid's pressure is observed. Because of this compression, which takes place almost adiabatically, the water contained in the system is heated up, and a temperature increase 31 is observed. The heat generated during the piston's jump movement is gradually absorbed by the walls of the piston chamber and the column tube. Heat absorption leads to a slow decrease 32 of the fluid's temperature.

When imposing a sudden backward movement onto the piston, the volume of water contained in the system is expanded, and a sudden pressure decrease 33 is obtained. Correspondingly, there is a sudden decrease 34 of the fluid's temperature. During the subsequent temperature equalization process, a slow increase 35 of the fluid's temperature is observed, with the fluid's temperature slowly approaching its equilibrium value.

When increasing the fluid's pressure by more than 400 bar (36), a significant temperature increase 37 is obtained. The temperature increase 37 causes a temperature-induced expansion of the volume of water contained in the system, which in turn gives rise to an additional temperature-induced contribution 38 to the fluid's total pressure. The temperature increase 37 is followed by a slow decrease 39 of the fluid's temperature, which is due to heat dissipation. In parallel with the slow decrease 39 of the fluid's temperature, the temperature-induced contribution to the fluid's total pressure also decreases. Hence, in synchronism with the temperature equalization process, a corresponding pressure relaxation 40 is obtained.

At a point of time 41, the fluid's pressure is increased (42) up to about 700 bar, and accordingly, there is a further temperature increase 43. Again, in parallel to the temperature decline 44, there is a corresponding relaxation 45 of the fluid's pressure.

At a point of time 46, a backward displacement is imposed onto the piston, a pressure drop 47 is observed, and the water contained in the system is cooled down (48). During a subsequent temperature equalization process 49, the fluid's temperature slowly rises and approaches its equilibrium value.

From FIG. 3, it can be seen that pressure-induced temperature changes ΔT range from 0.16 to 0.19° C. per 100 bar pressure change. Hence, with regard to water, both the temperature changes and the temperature-induced pressure contributions remain rather small and do not significantly disturb the accuracy of a metering device.

Figure 4A:
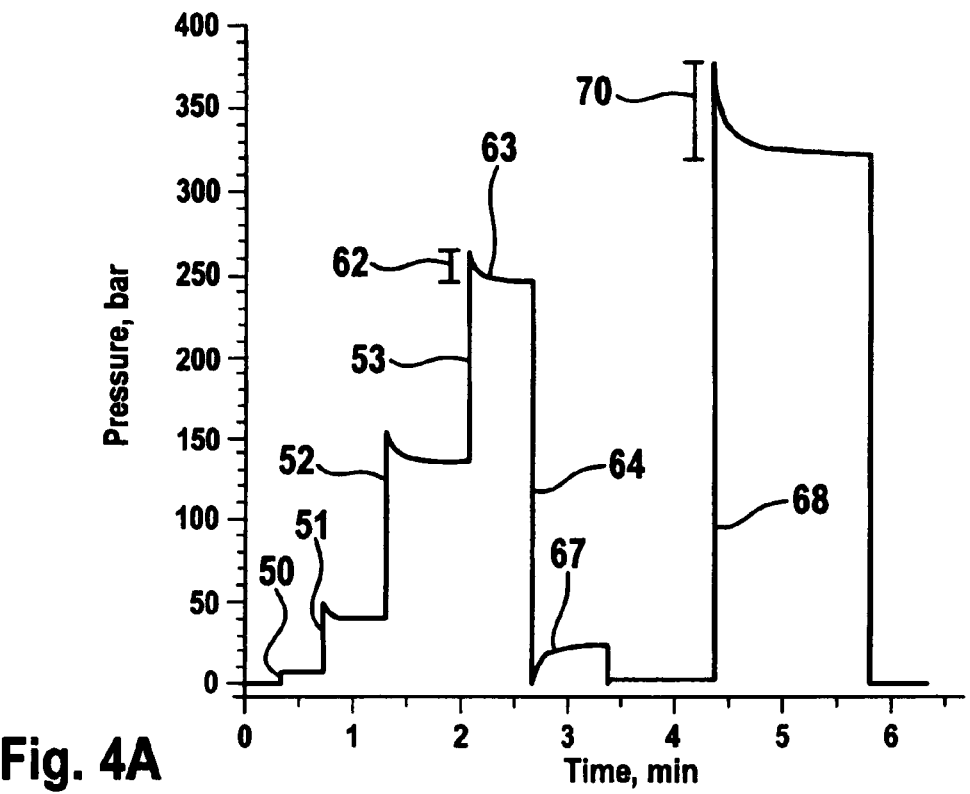
Figure 4B:
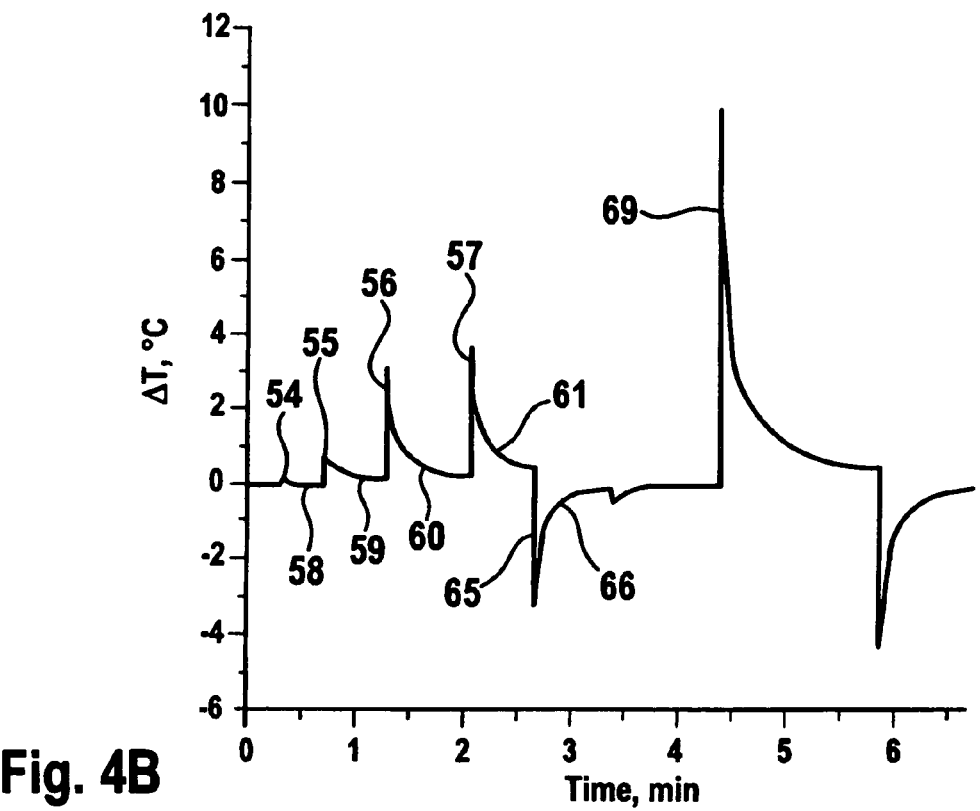

FIGS. 4A and 4B show results that have been obtained for methanol. Here, the effects are more pronounced. FIG. 4A shows the fluid's pressure (in bar) versus time (in minutes), and FIG. 4B shows related temperature changes ΔT (in ° C.) versus time. The measurement results have been obtained using the measurement set-up of FIG. 2. During each one of the compression jumps 50, 51, 52, 53, a corresponding temperature increase 54 to 57 is observed. Each temperature increase 54 to 57 leads to an additional thermal expansion of the fluid and hence to a temperature-induced pressure contribution. For example, the temperature increase 57 causes a pressure contribution 62. Each temperature increase 54 to 57 is followed by a subsequent temperature relaxation 58 to 61, and by a corresponding pressure relaxation. For example, during the temperature relaxation 61, a corresponding pressure relaxation 63 is obtained.

A pressure drop 64 is obtained by imposing a sudden expansion onto the volume of fluid in the metering device. Because of the expansion, the temperature of the fluid decreases (65). The sudden temperature decrease 65 is followed by a slow temperature equalization 66. The slow temperature equalization 66 gives rise to a corresponding relaxation 67 of the temperature-induced pressure contribution.

A pressure increase 68 of about 320 bar leads to a corresponding temperature increase 69 of more than 8° C., which in turn gives rise to an additional pressure contribution 70 with a magnitude of approximately 50 bar. Hence, in case of methanol, the effects due to temperature variations are likely to cause significant errors. For example, the additional solvent flow that is due to temperature-induced expansion or contraction of the solvent might impair a metering device's precision.

TABLE 1

| Solvent | Temperature increase per 100 bar (in ° C.) | Adiabatic overpressure per 100 bar end pressure (in bar) |
|---|---|---|
| Water | 0.16-0.19 | 4-7 |
| Methanol (MeOH) | 2-2.8 | 14-18 |
| Acetonitrile (ACN) | 2-3 | 30-45 |
| Hexane | 2-3 | 25-28 |

Table 1 shows results that have been obtained by characterizing the solvents water, methanol (MeOH), acetonitrile (ACN), and hexane. The second column indicates the temperature increase per 100 bar pressure change in degree Celsius. In case of water, the temperature increase is rather small (0.16 to 0.19° C./100 bar), but for the other solvents, a temperature increase between 2 and 3° C. per 100 bar pressure change is obtained. As explained above, the pressure increase leads to an additional contribution to the solvent's pressure. At the end of the adiabatic compression, the solvent's pressure looks higher than it actually is, which is due to the temperature increase.

The third column of table 1 indicates adiabatic overpressure (in bar) per 100 bar end pressure. With regard to water, the pressure contribution is quite small, but for methanol, hexane, and especially for acetonitrile, the effects are much more pronounced. In fact, for acetonitrile, up to 45 bar overpressure may be obtained per 100 bar end pressure. Though these results are to be considered as preliminary, they give a clear idea of the flow error sources upon compressing a volume of solvent in a piston chamber.

Figure 5:
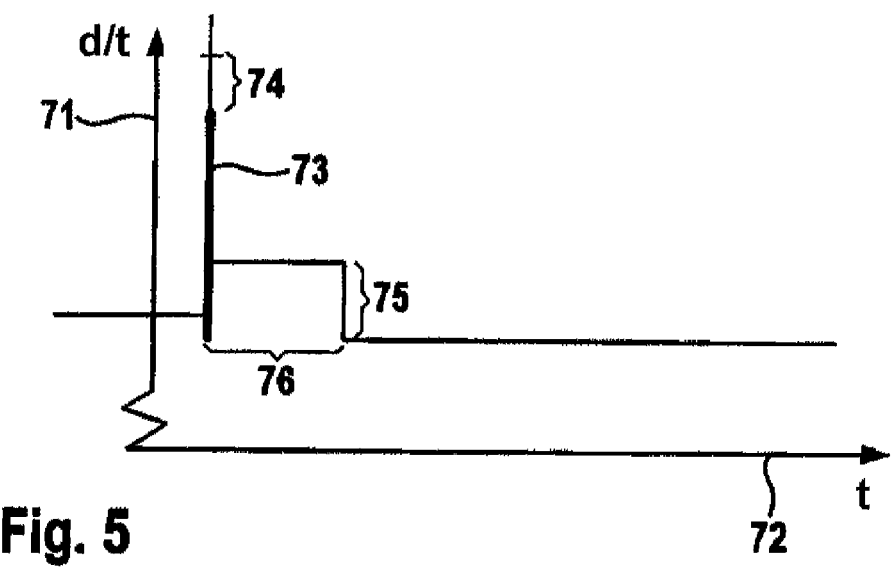
FIG. 5 illustrates a corrective movement superposed onto the piston movement.

FIG. 5 shows how to superpose a corrective movement onto the piston's displacement rate, in order to compensate for thermal expansion and/or contraction related to a temperature change and to a subsequent temperature equalization process. Axis 71 indicates the piston's displacement rate, and axis 72 is a time axis. Peak 73, which indicates a sudden increase of the piston's displacement rate, relates to a compression jump. The compression jump induces a temperature increase, which in turn gives rise to a corresponding thermal expansion. In order to compensate for the additional thermal expansion related to the temperature increase, it is proposed to reduce (74) the magnitude of the peak 73. Thus, it is taken into account that the heat generated during the fluid's compression provides a contribution to the fluid's total pressure.

Subsequent to the temperature increase, heat dissipates through the walls of the pump chamber. The fluid's temperature slowly decreases, and as a consequence, a slow thermal contraction of the fluid is observed. In order to counteract this slow thermal contraction, the piston's forward movement is accelerated by increasing (75) the piston's displacement rate during a predefined period of time 76. This additional forward displacement compensates for the thermal contraction that is due to the temperature equalization process.

Hence, the corrective movement imposed onto the piston movement comprises two components: a reduction 74 of the compression jump, and a subsequent increase 75 of the piston's forward displacement during a period of time 76. The reduction 74 of the compression jump compensates for the fluid's thermal expansion. The increase 75 of the piston's forward displacement during the period of time 76 compensates for the fluid's subsequent thermal contraction, with the period of time 76 corresponding approximately to the time required for the temperature equalization process.

Figure 6:
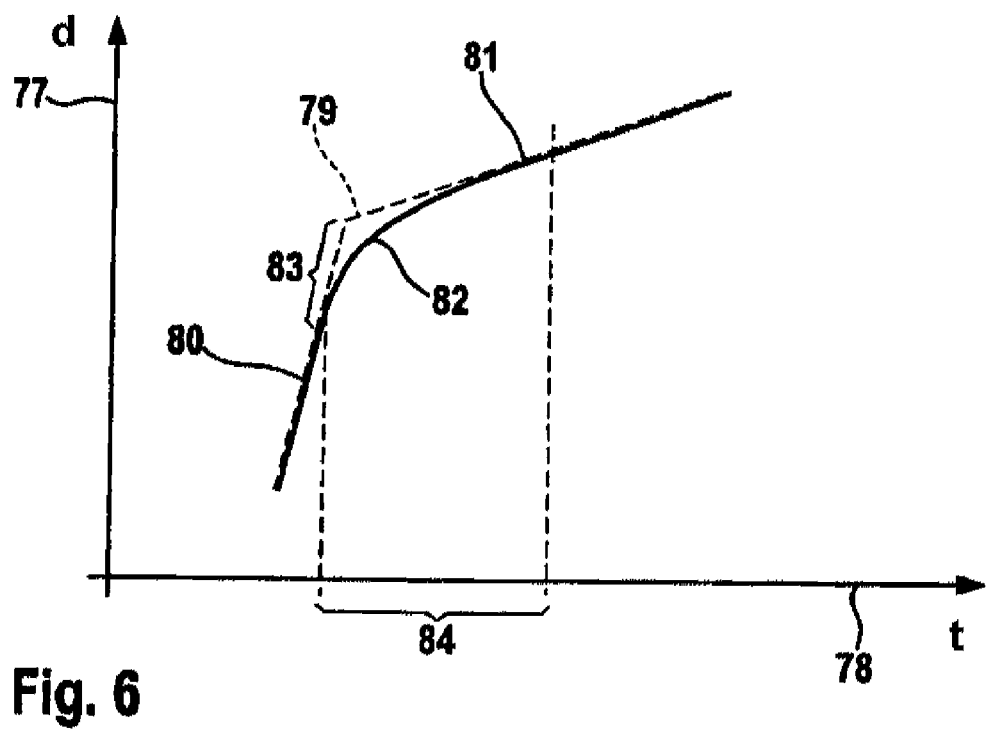
FIG. 6 shows both the non-corrected and the corrected piston displacement as a function of time.

FIG. 6 shows the piston's position as a function of time both for the non-corrected piston movement and for the corrected piston movement. Axis 77 indicates the piston's position, and axis 78 is a time axis. The dashed curve 79 relates to the non-corrected piston movement. First, there is a compression jump 80, and then, the piston is moved forward (81) at a constant displacement rate. Curve 82 relates to the corrected displacement of the piston as a function of time. Correcting for temperature induced effects comprises reducing the compression jump 80 by a certain amount 83. Correcting for temperature-induced effects further comprises superposing, during a time interval 84, an additional forward displacement onto the piston movement. This additional forward displacement is intended to compensate for the fluid's pressure relaxation. After the time interval 84 has elapsed, the corrected curve 82 is substantially equal to the non-corrected curve 79. According to embodiments of the present invention, it is proposed to control the piston's forward movement in accordance with the corrected curve 82.

The corrective movements superposed onto the piston movement may comprise both a reduction 74 of the piston's compression jump and a subsequent increase 75 of the piston's forward displacement rate. Alternatively, one might only superpose one of those two corrective movements onto the piston. For example, according to an alternative embodiment, only the magnitude of the compression jump is reduced, in order to compensate for the temperature-induced thermal expansion. According to yet another embodiment, the magnitude of the compression jump is not modified, but the thermal contraction is compensated for by increasing the piston's forward displacement rate during the process of temperature equalization.

Figure 7A:
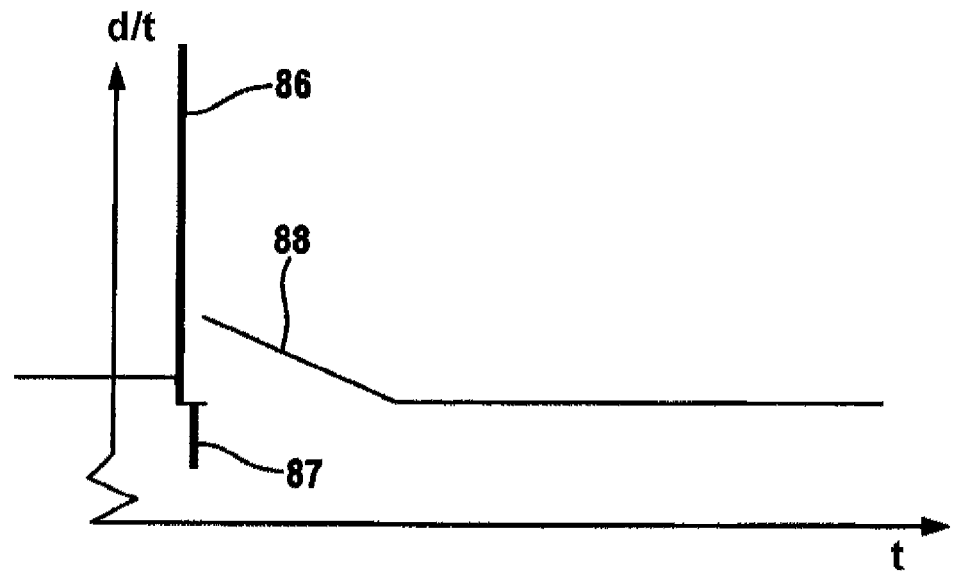
Figure 7B:
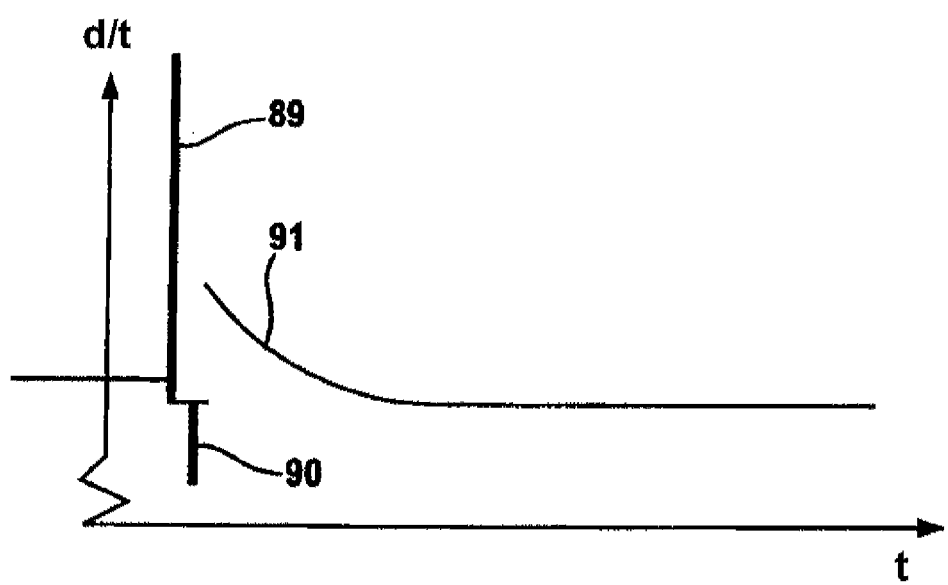

In FIG. 5, the correction imposed onto the piston movement has been of rectangular shape. FIGS. 7A and 7B show further alternative embodiments for realizing a corrective movement. In FIG. 7A, instead of decreasing the magnitude of the compression jump 86, an expansion jump 87 is executed, with the expansion jump 87 compensating for the fluid's thermal expansion. Then, in order to counteract the subsequent slow thermal contraction, the piston's forward displacement rate is increased by superposing a correction 88 of triangular shape onto the piston's movement. FIG. 7B shows a further alternative embodiment for correcting the piston movement. Again, the compression jump 89 is followed by an expansion jump 90. Then, the subsequent slow thermal contraction is counteracted by superposing an exponentially declining additional displacement 91 onto the piston movement.

Figure 8:
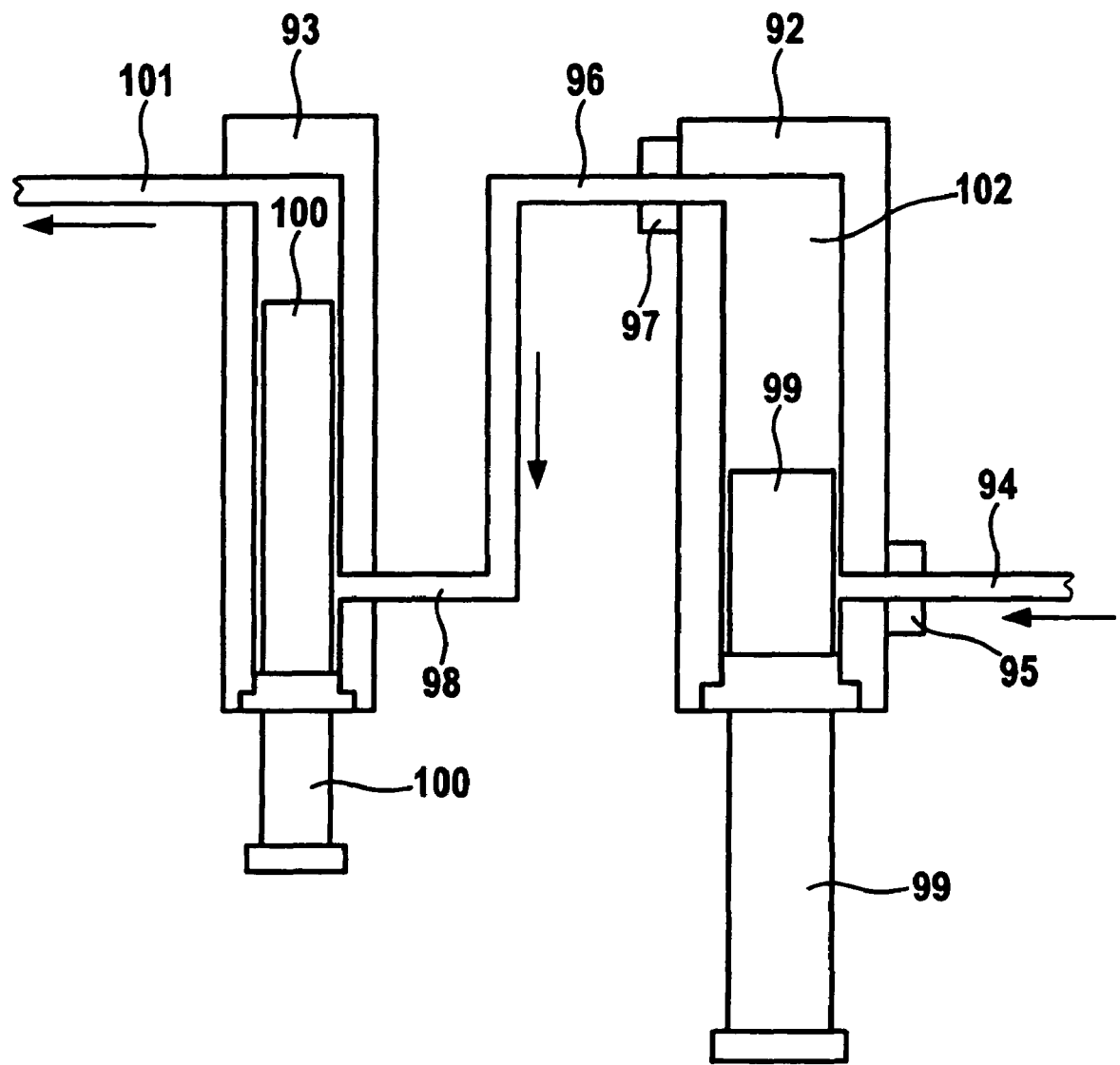
FIG. 8 shows an arrangement of two pump heads fluidly connected in series.

In the solvent supply system shown in FIG. 1A, each of the fluid supply paths 1, 3 comprises one high pressure pump. However, in order to provide for a constant flow of solvent, an arrangement of two pump heads as shown in FIG. 8 can be used instead of a single metering device. The arrangement shown in FIG. 8 comprises a primary pump head 92 and a secondary pump head 93 that is connected in series with the primary pump head 92. The primary pump's inlet 94 is equipped with an inlet valve 95, and the outlet 96 is equipped with an outlet valve 97. The outlet 96 is in fluid communication with the inlet 98 of the secondary pump.

During a first phase of operation, the primary pump's piston 99 is moved downwards, whereas the secondary pump's piston 100 performs an upward stroke. During the first phase of operation, the inlet valve 95 is opened, and the outlet valve 97 is shut. During the downward stroke of the primary pump's piston 99, solvent at atmospheric pressure is aspirated via the inlet 94. Simultaneously, the secondary pump's piston 100 performs an upward movement and supplies a flow of solvent at a pressure of several hundred or even several thousand bar at the secondary pump's outlet 101.

During a subsequent second phase of operation, the primary pump's piston 99 is moved in the upwards direction, whereas the secondary pump's piston 100 performs a downward movement. The upward movement of piston 99 comprises compressing the volume of fluid 102 contained in the primary pump's pump chamber from atmospheric pressure to a pressure of up to several thousand bar. When the required pressure is reached, the outlet valve 97 opens, and during the subsequent upward movement of piston 99, solvent at high pressure is supplied at the primary pump's outlet 96. The primary pump's piston 99 displaces about twice the volume of the secondary pump's piston 100. For this reason, the downward stroke of piston 100 is overcompensated by the upward stroke of piston 99, and hence, a resulting flow of solvent is obtained at the secondary pump's outlet 101.

FIG. 9 shows four different curves 103 to 106 that indicate the displacement of the primary pump's piston 99 as a function of time during the piston's upward stroke. Axis 107 indicates the piston's displacement, and axis 108 is a time axis. Each of the four curves 103 to 106 comprises an initial compression jump 109 followed by a continuous forward movement 110 of the piston 99. During the compression jump 109, the fluid's pressure is increased from atmospheric pressure to a pressure of up to several thousand bar. As soon as system pressure is reached, the outlet valve 97 opens up, and the primary pump starts supplying fluid at a constant rate.

The four curves 103 to 106 shown in FIG. 9 differ by the magnitude of their respective compression jump 109. In curves 103 and 104, the magnitude of the respective compression jump is not sufficient for bringing the fluid to system pressure. Curve 103 will further on be referred to as "strong undercompensation", and curve 104 will be referred to as "slight undercompensation". Curve 105 relates to the case of "nearly correct compensation". This means that the pressure reached at the end of the compression jump of curve 105 is nearly equal to system pressure. Hence, in curve 105, the magnitude of the compression jump is as large as it should be. In curve 106, the magnitude of the compression jump is too large: The pressure reached at the end of the compression jump is larger than system pressure. Therefore, the outlet valve 97 already opens up during the compression jump.

FIG. 10 shows four different pressure-versus-time curves 111 to 114 that correspond to the four displacement-versus-time curves 103 to 106, respectively. Curve 111 relates to the case of "strong undercompensation", curve 112 relates to "slight undercompensation", curve 113 relates to "nearly correct compensation", and curve 114 relates to "overcompensation". A first portion 115 of each of the curves 111 to 114 corresponds to the primary pump's upward stroke, respectively. At the end of the primary pump's upward stroke, there is a discontinuity, and then, during a second portion 116 of the pressure curves, fluid is supplied by the secondary pump. The second portion 116 of the pressure curves relates to the secondary pump's upward stroke, respectively.

Curve 114 relates to "overcompensation". In case of overcompensation, the piston's compression jump is too large (cf. curve 106), and therefore, curve 114 comprises a large pressure peak 117. Pressure peak 117 is followed by a subsequent pressure relaxation, which is partly due to temperature equalization. The heat generated during the compression jump is slowly absorbed by the walls of the piston chamber, and the fluid contained in the pump chamber is slowly cooled down.

Pressure curve 113 corresponds to the case of "nearly correct compensation", and to curve 105 of FIG. 9. Pressure curve 113 comprises a peak 118 related to thermal expansion during the compression jump. Peak 118 is followed by a slow pressure relaxation 119 that is due to a thermal equalization process.

Curve 111, which relates to the case of "strong undercompensation", shows an initial pressure drop 120. However, also in curve 111, there is a positive pressure contribution related to the temperature increase during compression. Without this positive pressure contribution, pressure drop 120 would be even more significant. Again, subsequent to the compression jump, a slow pressure relaxation 121 is observed.

Figure 11:
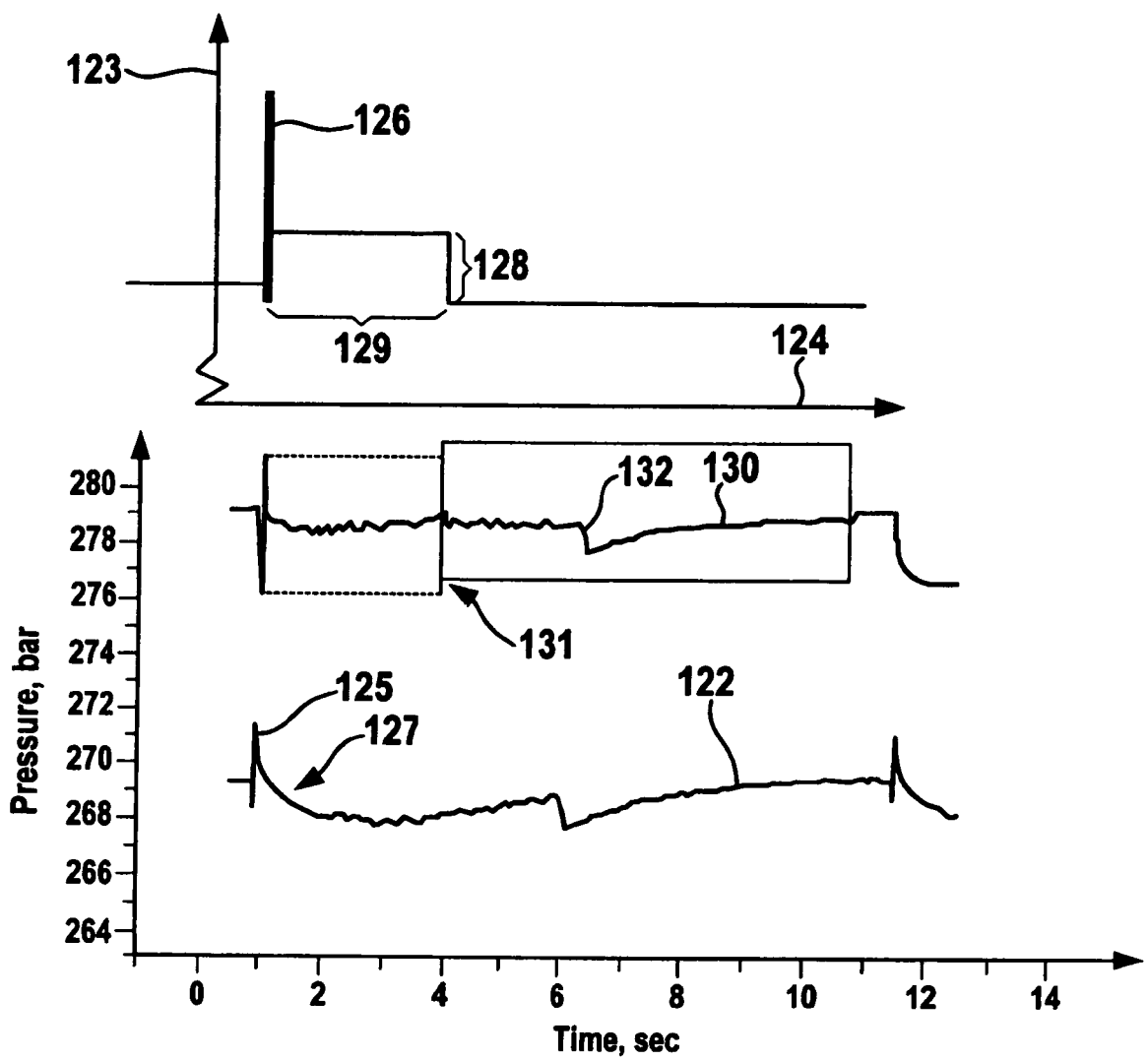
FIG. 11 illustrates how superposing a corrective movement onto the piston movement alters the pressure curve.
Figure 12:
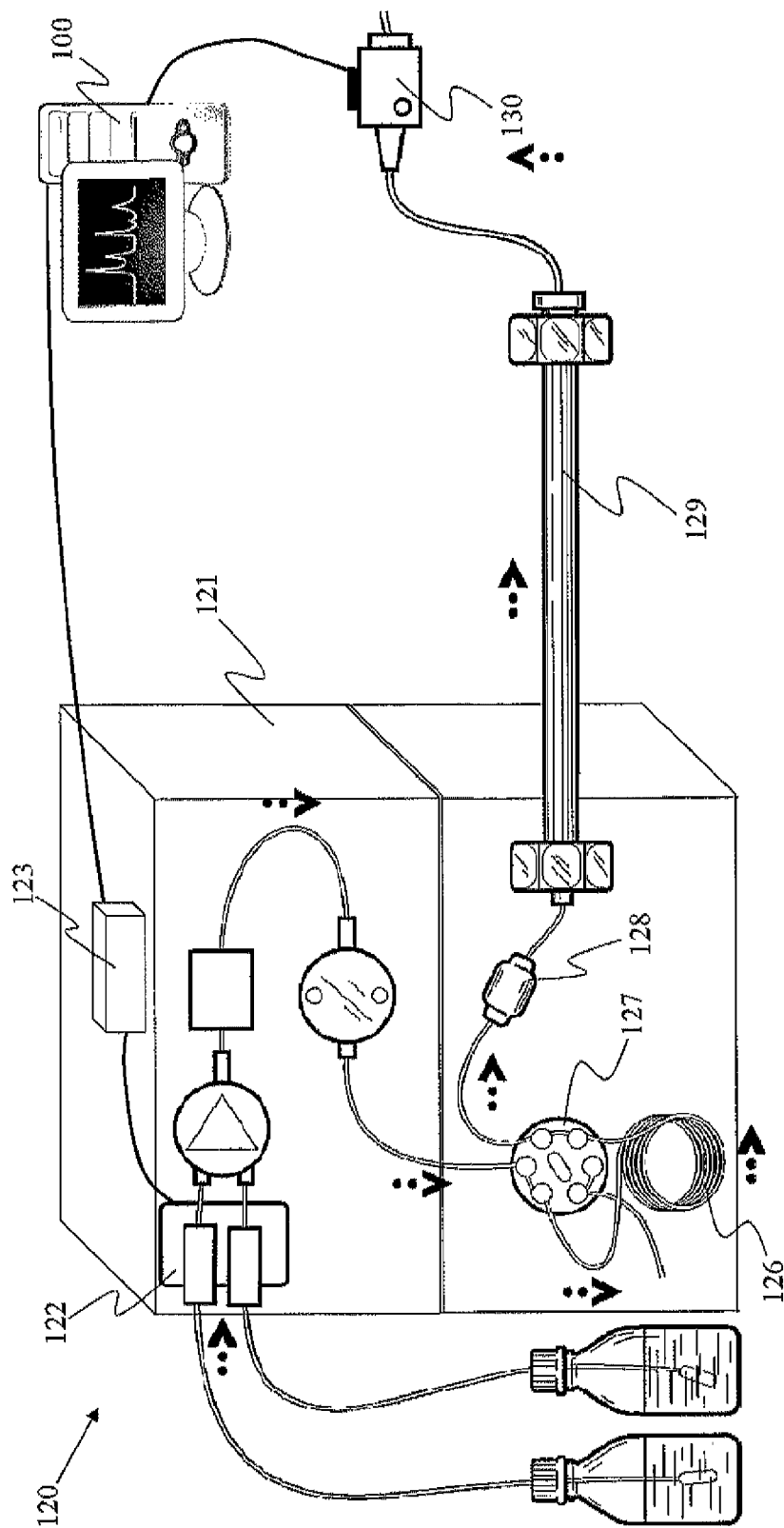
FIG. 12 shows a known liquid chromatography system.

FIG. 11 shows a pressure-versus-time curve 122 that has been acquired before the piston movement has been subjected to any kind of correction. The diagram in the upper part of FIG. 11 shows a corrective movement superposed onto the piston movement, with axis 123 indicating the displacement rate, and with axis 124 being a time axis. For removing the pressure increase 125 that is due to the compression jump, the magnitude of the compression jump 126 is reduced. Furthermore, a slow pressure drop 127 related to the temperature equalization process is counteracted by increasing (128) the piston's displacement rate during a time interval 129.

Pressure curve 130 indicates pressure as a function of time after the piston movement has been corrected in accordance with the diagram shown in the upper part of FIG. 11. In the pressure curve's first portion 131, which corresponds to the primary pump's upward stroke, both the pressure increase 125 and the subsequent pressure drop 127 have been compensated for.

Compared to pressure curve 122, pressure variations are significantly reduced, and the pressure curve's first portion 131 almost looks like a straight line. In fact, in pressure curve 130, pressure is almost kept constant, with the only discontinuity 132 being due to the piston's change of direction. This implies that flow variations are considerably reduced as well. The metering device is therefore capable of supplying fluid at a very precise flow rate. Furthermore, in fluid supply systems that provide a composite solvent with a certain mixing ratio of two or more different solvents, or in systems that supply a solvent gradient, the composite solvent's mixing ratio can be adjusted more precisely than before.

The invention claimed is:

1. A method for controlling movement of a piston in a metering device, the method comprising
   supplying a fluid by actuating the piston, wherein compression or expansion of the fluid, which is caused by piston movement, causes corresponding temperature variations,
   superposing a corrective movement onto the piston movement, with the corrective movement at least partly compensating for at least one of thermal expansion and contraction of the fluid induced by the temperature variations, wherein the corrective movement comprises a backward displacement to at least partly compensate for the thermal expansion related to a temperature increase, and
   wherein at least one of a magnitude and a time behavior of the corrective movement is dependent on the type of solvent contained in the pump chamber.

2. The method of claim 1, wherein the corrective movement is adapted for at least partly compensating for at least one of: temperature-induced flow variations and temperature-induced pressure variations of the fluid.

3. The method of claim 1, wherein
   the temperature variations in the pump chamber comprise a temperature change related to compression or expansion of the fluid in the pump chamber, wherein the temperature change gives rise to a thermal expansion or contraction related to the temperature change;
   the temperature variations in the pump chamber comprise a temperature equalization process that occurs as a consequence of the temperature change, wherein the temperature equalization process gives rise to a thermal expansion or contraction related to the temperature equalization process;
   the temperature variations occur periodically during each duty cycle of the metering device; or
   a temperature increase that is due to a compression of the fluid in the pump chamber during the piston's downwards stroke gives rise to a corresponding thermal expansion and to a subsequent thermal contraction.

4. The method of claim 1, further comprising at least one of:
   counteracting a thermal expansion or contraction related to a temperature change that is due to a compression or expansion of the fluid in the pump chamber by superposing a corresponding corrective movement onto the piston movement; or
   counteracting a thermal expansion or contraction related to a temperature equalization process that occurs subsequently to a temperature change by superposing a corresponding corrective movement onto the piston movement.

5. The method of claim 1, further comprising at least one of
   superposing an additional forward displacement onto the piston movement during a predefined period of time in order to at least partly compensate for a thermal contraction that is due to a temperature equalization process, wherein the predefined period of time substantially corresponds to a time required for the temperature equalization process;
   superposing one of a constant forward displacement rate, a triangular forward displacement rate, an exponentially declining forward displacement rate onto the piston movement during a predefined period of time, in order to at least partly compensate for a thermal contraction that is due to a temperature equalization process; or
   adjusting the time behavior of the corrective movement in dependence on an internal geometry of the pump chamber.

6. A system comprising a control unit for controlling movement of a piston in a metering device,
   wherein compression or expansion of a fluid, which is caused by piston movement in a pump chamber of the metering device, causes corresponding temperature variations,
   wherein the control unit is adapted for superposing a corrective movement onto the piston movement, with the corrective movement at least partly compensating for at least one of thermal expansion and contraction of the fluid induced by the temperature variations, wherein the corrective movement comprises a backward displacement to at least partly compensate for the thermal expansion related to a temperature increase, and wherein at least one of the magnitude and the time behavior of the corrective movement is dependent on the type of solvent contained in the pump chamber.

7. The system of claim 6, wherein the temperature variations in the pump chamber comprise a temperature change related to compression or expansion of the fluid in the pump chamber;

the temperature variations in the pump chamber comprise a temperature equalization process that occurs as a consequence of the temperature change; or the corrective movement superposed onto the piston movement is adapted for counteracting a thermal expansion or contraction related to at least one of a temperature change that is due to a compression or expansion of the fluid in the pump chamber, and a temperature equalization process that occurs subsequently to a temperature change.

8. The system of claim 7, the system being adapted for metering a fluid, the system further comprising:

a first piston adapted for metering the fluid, wherein compression or expansion of the fluid in the pump chamber causes corresponding temperature variations, and a second piston, wherein the control unit is adapted for imposing a corrective movement onto the second piston's movement, with the corrective movement at least partly compensating for at least one of thermal expansion and contraction of the fluid induced by the temperature variations.

9. The system of claim 6, wherein the system is adapted for supplying a fluid at a pressure between 200 and 2000 bar;

the system comprises a single piston pump;

the system comprises a dual piston pump with a primary piston pump and a secondary piston pump, the primary piston pump and the secondary piston pump being fluidically connected in series;

the primary piston pump is adapted for compressing the fluid in its pump chamber from atmospheric pressure to a pressure of about 200 bar to 2000 bar; or the system comprises a tandem pump with two piston pumps being fluidically connected in parallel.

10. The system of claim 6, further comprising a first solvent supply flow path with a first metering device, the first supply flow path being adapted for supplying a first solvent to a mixing unit;

a second solvent supply flow path with a second metering device, the second supply flow path being adapted for supplying a second solvent to the mixing unit;

the mixing unit being adapted for mixing the first and the second solvent and for supplying a composite solvent with a mixing ratio of the first and the second solvent.

11. The system of claim 10, wherein the control unit is adapted for controlling a piston movement of the first metering device and a piston movement of the second metering device such that the mixing ratio becomes substantially independent of temperature variations;

the control unit is adapted for counteracting at least one of thermal expansion and contraction induced by temperature variations by superposing a compensatory movement onto at least one of a piston movement of the first metering device and a piston movement of the second metering device;

the control unit is adapted for such controlling a piston movement of the first metering device and a piston movement of the second metering device that the composite solvent is provided at a constant flow rate;

the system is adapted for supplying a composite solvent at a pressure between 200 and 2000 bar;

the system is implemented as a part of a microfluidic device;

the system is adapted for supplying a composite solvent to a separation system adapted for separating compounds of a fluid sample;

an outlet of the mixing unit is connected with an inlet of a separation system;

the composite solvent is used as a mobile phase for separating compounds of a fluid sample; or the separation system is one of: a liquid chromatography system, an electrophoresis system, an electro chromatography system.

12. A software program, embodied on a non-transitory computer readable medium, for executing the method of claim 1, when run on a data processing system.

* * * * *